United States Patent [19]

Karg et al.

[11] 4,036,241

[45] July 19, 1977

[54] FILM-FORMING CARBOXY-CONTAINING RESIN AND A POLYVALENT METAL SALT IN A HAIR SPRAY AND A METHOD OF USING THE SAME

[75] Inventors: Gerhart Karg, Pompton Lakes, N.J.; Christopher D. Vaughan, Greenwood Lake, N.Y.

[73] Assignee: Avon Products, Inc., Suffern, N.Y.

[21] Appl. No.: 618,469

[22] Filed: Oct. 1, 1975

[51] Int. Cl.$^2$ .......................... A45D 7/00; A61K 7/11
[52] U.S. Cl. ........................................ 132/7; 8/127.51;
260/23 AR; 260/29.6 MM; 260/33.4 R;
260/33.8 UA; 424/DIG. 1; 424/DIG. 2;
424/47; 424/71; 424/78; 424/81
[58] Field of Search ................. 424/DIG. 1, DIG. 2,
424/47, 71, 78, 81; 132/7; 8/127.51; 260/23
AR, 29.6 MM, 33.4 R, 33.8 UA

[56] References Cited

U.S. PATENT DOCUMENTS

| 2,723,248 | 11/1955 | Wright .................................. 424/47 |
| 3,630,654 | 12/1971 | Rosenthal et al. ................. 424/71 X |
| 3,723,616 | 3/1973 | Erlemann et al. ..................... 424/47 |
| 3,800,033 | 3/1974 | Flawn et al. ....................... 424/71 X |
| 3,846,384 | 11/1974 | Doe ................................... 424/71 X |
| 3,850,178 | 11/1974 | Schoenholz ....................... 424/71 X |

*Primary Examiner*—Sam Rosen
*Assistant Examiner*—Vera C. Clarke
*Attorney, Agent, or Firm*—Pennie & Edmonds

[57] ABSTRACT

A hair spray composition comprising an alcoholic medium having substantially uniformly dispersed therein a film forming carboxylic acid containing resin and a polyvalent metal alkyl carboxylic acid salt having from 5 to 20 carbon atoms, said composition having a pH from about 3.5 to 7.5.

20 Claims, No Drawings

FILM-FORMING CARBOXY-CONTAINING RESIN AND A POLYVALENT METAL SALT IN A HAIR SPRAY AND A METHOD OF USING THE SAME

BACKGROUND OF THE INVENTION

The present invention relates to hair spray compositions and, particularly, to hair spray compositions which are suitable for aerosol application.

Substances which are suitable candidates for use as a hair spray composition must fulfill a number of requirements. They must form glossy, clear films which are capable of adhering to the hair fiber. Further, they must have good solubility in the solvent media with which they are associated. The film which is formed on the hair must be sufficiently flexible to hold the hair in place permanently despite the usual agitation attributable to wind and movement of the head yet the film must be sufficiently stiff to allow the hair to be combable without collapsing.

In addition, substances utilized must form a film which, on one hand, must be water-soluble or at least capable of swelling under the action of water to be removable by ordinary shampooing methods and which, on the other hand, must be substantially uneffected by water vapor even at high relative humidity.

It is clear that the requirements set forth for hair spray compositions have built within them certain diametrically opposed properties which make a large number of apparently potential compositions unsuitable for such use.

For example, many polymer compositions heretofore used have the desired solubility properties are highly hygroscopic and, therefore, give the hair a sticky feel at relatively high humidity. Some polymers which are substantially non-hygroscopic exhibit unsatisfactory solution properties. Still other compositions have good hygroscopicity and solution properties but are difficult to remove from the hair which, therefore, causes an undesired build-up of the composition on the hair.

Further, hair spray compositions are presently commonly applied to the hair by aerosol technique. Aqueous compositions are generally excluded from being packaged with conventional aerosol containers and propellants due to container corrosion problems caused by such compositions as well as stability problems of propellants, especially halogenated hydrocarbons, with the water of the composition.

Polymeric systems which have been previously proposed include carboxy-containing copolymers such as disclosed in U.S. Pat. Nos. 2,723,248 and 3,723,616. These polymers are made washable from the hair by neutralizing the polymer with a lower molecular weight hydroxy-containing amine, such as diethanolamine or aminomethyl propanediol. Such products have increased moisture sensitivity and, thus, are of little aid in retaining the shape of the hair during periods of high humidity. U.S. Pat. No. 3,850,178 is also directed to hair setting compositions which utilize carboxy-containing resins in combination with a complex formed from a polyvalent metal compound and an alkaline compound. The highly alkaline pH of the composition can be harmful to the hair, possibly causing degradation thereto. Further, the composition requires the use of an aqueous carrier which effectively restricts the utility of the composition to non-aerosol applications due to corrosion and stability problems.

SUMMARY OF THE INVENTION

The present invention is directed to hair spray compositions which form clear, glossy films when applied to the hair and which aid in retaining the desired shape given to the hair. The films are substantially non-sensitive to atmospheric humidity yet are capable of removal by any conventional aqueous shampoo solution. The alcoholic composition of the present invention do not present stability or corrosion problems when applied by conventional aerosol packaging using conventional halogenated hydrocarbon propellants.

The compositions of the present invention comprise an alcoholic medium having substantially uniformly distributed therein a film-forming carboxy-containing resin and a polyvalent metal salt of a $C_5$-$C_{20}$ alkyl carboxylic acid; said composition having a pH of from about 3.5 to 7.5.

DETAILED DESCRIPTION

The hair spray composition of the present invention is uniquely suited for aerosol application to the hair as it forms a stable alcoholic solution of the resin and acid salt described hereinbelow.

The resin component of the present invention is a film-forming polymeric material which is soluble in a $C_1$-$C_8$ alcohol. The polymeric material must contain at least 5% by weight free carboxylic acid groups. The preferred free carboxylic acid content will vary according to the degree of hardness and adhesiveness desired and, in general, amounts of greater than 10% by weight of the resin are preferred.

Resins which are suitable for use in the present composition include copolymers of monomeric unsaturated carboxylic acids or acid anhydrides with comonomers capable of producing a resin soluble in a $C_1$-$C_8$ alcohol. Examples of preferred resins are copolymers of alkyl vinyl ethers and maleic anhydrides; copolymers of $C_2$-$C_6$ alkene compounds and maleic anhydrides and copolymers formed from vinyl esters and an acrylic acid.

The copolymers of an alkyl vinyl ether with the half-ester of maleic anhydride are the most desired copolymers for use in the present invention. Alkyl vinyl ethers useful in forming the present copolymer have alkyl substituents containing 1 to 4 carbon atoms, such as methyl vinyl ether, ethyl vinyl ether, propyl vinyl ether, isopropyl vinyl ether, butyl vinyl ether, and isobutyl vinyl ether with methyl vinyl ether being preferred. The alkyl vinyl ether is copolymerized with a sufficient amount of maleic anhydride to form a copolymer which, after being half esterified, contains at least 5%, and preferably at least 10%, by weight of the resultant resin as free carboxylic acid groups. The half-ester can be a $C_1$-$C_5$ alkyl ester of the acid.

The alkyl vinyl ether-maleic anhydride half ester copolymers may be prepared by initially polymerizing the ether and anhydride and esterifying the resultant polymer by known methods such as described in U.S. Pat. No. 2,047,398, the teaching of which is incorporated herein by reference. Examples of preferred copolymers of this type are poly(methyl vinyl ether/maleic anhydride half ethyl ester), poly(methyl vinyl ether/maleic anhydride half butyl ester) and poly(propyl vinyl ether/maleic anhydride half ethyl ester).

The second class of copolymers found useful in forming the hair setting composition of the present invention are copolymers which are $C_2$-$C_6$ alkene/maleic anhydride half-$C_1$-$C_5$ alkyl ester. The $C_2$-$C_6$ alkene compound useful in forming the copolymer herein include ethylene, propylene, butylene, isobutylene, 1-hexene, neohexene and butadiene. The copolymer is formed in conventional manners well known to those skilled in the art, such as by initially copolymerizing the alkylene and anhydride compounds with a standard free radical initiator and esterifying the resultant polymer to form a $C_1$-$C_4$ alkyl ester. The resultant copolymer should have at least 5% free carboxylic acid groups based on the weight of the resin. Illustrative examples of this class of resin include poly(hexene/maleic anhydride half ethyl ester), poly(ethylene/maleic anyydride half ethyl ester) and poly(ethylene/maleic anhydride half butyl ester).

The third class of resins found useful in forming the hair setting composition of the present invention are copolymers of a vinyl ester and acrylic acid or a substituted derivative thereof. The vinyl ester may be, by way of example, vinyl acetate, vinyl propionate, vinyl butylate, and the like. Acids useful in forming the copolymer are acrylic acid or an alpha or beta substituted $C_1$-$C_3$ alkyl acrylic acid, such as, for example, α-methylacrylic acid, β-methyl acrylic acid, α-ethyl acrylic acid, β-ethylacrylic acid, α-isopropylacrylic acid, and the like. Examples of copolymers of this class include poly(vinyl acetate/crotonic acid), poly(vinyl acetate/methacrylic acid), and poly(vinyl acetate/acrylic acid).

The film-forming, carboxy-containing resins described hereinabove are utilized in the alcoholic medium hereinabove in combination with a $C_5$-$C_{20}$ carboxylic acid salt of a polyvalent metal. The salt may be formed from any polyvalent metal capable of forming metal salt linkages with the carboxylic acid moiety of the resin. While most polyvalent metals will react with the carboxylic acid carboxylic acid moieties of the resin, not all will be totally acceptable for the present utility. Certain metals, such as cadmium, mercury, and copper are unduly toxic to be presently suitable while metals, such as iron, have a tendency to produce a colored film. The salts of zinc, zirconium, calcium, and magnesium are preferred as they form stable, non-toxic, clear, glossy films with the resins described hereinabove. The fatty acid salts are formed from a straight or branched chain monocarboxylic acid having from 5 to 20 carbon atoms therein. Examples of these acids include valeric, isovaleric, caproic, heptylic, caprylic, pelargonic, capric, lauric, myristic, palmitic, and stearic acids. In addition, the acid may be a branched chain $C_5$-$C_{20}$ monocarboxylic acid, such as, for example, 2-ethylhexanoic acid, neohexanoic acid, neoheptanoic acid, neodecanoic acid, 2-ethyl heptanoic acid, 2-octyldodecanoic acid, and the like. The branched chain acids are preferred due to their increased solubility in the alcoholic medium.

Any of the conventional methods for forming metal salts of carboxylic acid which are well known to those skilled in the art may be utilized to form the polyvalent metal salt of the monocarboxylic acid found useful in the present invention. The particular method for forming these materials is not deemed to be part of the subject invention.

The resin and carboxylic acid salt components described hereinabove are combined in an alcoholic medium to form the composition of the present invention. The alcohol may be any alcohol which is liquid at room temperature, such as a $C_1$-$C_8$ alcohol. Examples include methanol, ethanol, propanol, butanol, isobutanol, t-butanol, 1-pentanol, 2-pentanol, 1-heptanol, 3-heptanol, and the like. In addition, the alcohols may be used in combination with one another is conventional manners for formulating compositions in which all of the components of the present invention are soluble. The preferred alcoholic medium is ethanol or mixtures of ethanol with other alcohols. In addition to the alcohol, other inert materials may be used in combination with the alcohol to form the solvent medium. These may include ethers, such as diethylether, dioxane, and the like.

The amount of the film-forming carboxylic acid resin component for the present composition may vary widely depending on the particular end use of the product. For example, where more "body" is desired in the hair, higher concentrations of resin are used than in compositions used for general hair styling. Generally, the composition should contain resin in an amount sufficient to form a hair retaining film. For most uses, this will range from about 1 to about 10 parts by weight of the resin, preferably from about 3 to 6 parts by weight, for each 100 parts by weight of the composition.

The amounts of organic acid salts of a polyvalent metal to be used in the subject composition should be sufficient so that the ratio of metal to free carboxylic acid of the polymer should be a stoichiometric ratio of from 1 to 10 to less than 1 to 1. The upper limit, therefore, of the concentration of the fatty acid salts should be less than 100% of the theoretical substitution of the available acid functions in the polymer. The preferable range is from 10% to 50% of the theoretical substitution, or can be expressed as a stoichiometric ratio from 1 to 10 to 1 to 2.

Although certain of the fatty acid salts described herein are normally not soluble within the alcohols found useful in the present invention, it has been unexpectedly found that by first incorporating the resin material into the alcoholic medium and then introducing the fatty acid salts to the medium a completely homogeneous solution can be obtained. The fatty acid salts are thus unexpectedly soluble in the alcoholic medium in which the resin is contained.

The composition formed has a resultant pH of between 3.5 and 7.5. Preferably, the pH of the final composition should be a natural pH attained by the combined components of between about 4 and 6 and most preferably from between 4.5 to 5.5 which is the natural pH of human hair. The pH of the composition can be adjusted to this range by the amount of polymeric carboxylic acid groups permitted to remain free.

The compositions of the present invention have been found to yield highly satisfactory and stable hair setting films which are substantially unaffected by atmospheric conditions including high relative humidities. The resultant films can be easily removed from the hair by use of any commercially available shampoo and is not dependent upon the pH of the shampoo. Therefore, either commercial alkaline or low pH shampoos which have essentially the pH of natural hair can be utilized to remove the films formed by the hair spray compositions of the present invention.

Other additives normally present in hair setting compositions, such as perfumes, plasticizers, emollients, lubricants, penetrants, and the like, may be incorporated into the present composition. Furthermore, buffering agents, surfactants, colorants, stabilizers, and the like may also be added to the composition of the present invention. These can be used in the usual amounts for their usual effects.

Although the subject invention has been described in terms of compositions which are useful in aerosol packaging, the subject composition can be applied to human hair in any known conventional methods, such as by hand or spray bottle application. Where corrosion and stability are not a problem, the composition may contain up to 10% of the solvent medium of water to decrease the rate of drying of the composition.

The compositions of the present invention are most preferably applied to the hair via conventional aerosol propellant packaging. The alcoholic composition of the present invention is exceptionally suitable for use in aerosol techniques and no special precautions need be taken with respect to types of containers, valves, and/or propellants which may be used in the packaging or dispensing of the present composition. Any conventional aerosol propellant may be used in combination with the composition of the present including the halogenated hydrocarbons such as those commonly known and sold under the trade name of Freon which include trichlorofluoromethane, dichlorodifluoromethane, chlorotrifluoromethane, dichlorofluoromethane, trichlorotrifluoroethane, dichlorotetrafluoroethane, and the like as well as methylene dichloride and the like. In addition, other propellants may be used alone or in combination with the halogenated hydrocarbons in a conventional manner to form propellant compositions. These additional propellants include, for example, propane, butane, nitromethane, carbon dioxide, nitrous oxide, nitrogen and the like. Generally, one or a mixture of propellants which are sufficiently soluble with the compositions of the present invention and can attain normal pressure for the emission of substantially all of the hair setting compositions in the container, may be employed.

The invention will be further described in connection with the following examples, which are set forth for purposes of illustration only and are not to be construed as a limitation of the present invention. Parts and percentages are by weight unless otherwise expressly indicated.

EXAMPLE 1

A hair spray composition was prepared by mixing 8 parts Gantrez ES-425 [1] resin in ethanol until a solution was formed. 1.35 parts zinc neodecanoate was added to the solution with additional ethanol to form 100 parts of composition.

[1] A GAF copolymer of poly(methyl vinyl ether/maleic anhydride butylated half-ester):acid number = 245-275 equivalent weight=230.

The composition was tested for curl retention, physical characteristic of film formed, moisture resistance, and ability of removal from hair by conventional shampooing.

The composition was applied to previously shaped hair by spraying the composition uniformly onto the hair for a 4 second period. The composition dried on the hair at room temperature. The hair samples were subjected to 90% relative humidity at room temperature (72° F) for a 60 minute period resulting in 93.5% curl retention.

In addition, the composition was sprayed on a clear glass plate, allowed to dry and observed for clarity and gloss. The sample produced a clear, glossy film.

Further, moisture resistance of the composition on the hair was tested by subjecting test hair tresses of standard length to a solution of the composition. Excess composition was removed, the hair allowed to dry at room temperature. The "stick" of hair is dipped into room temperature water bath for 10 seconds which time permits only the film of composition to be affected and then horizontally positioning the treated hair sample and measuring the time period needed to cause a 2-inch drop from horizontal by the tip of the hair. Periods of from 2 to 4 minutes were deemed good; 4 to 7 minutes were deemed very good; 7 to 9 minutes were deemed excellent. No test was run for more than 9 minutes. The present composition exhibited good moisture resistance.

The sample was easily removed by a commercial hair shampoo.

EXAMPLE 2

The composition of Example 1 was packaged in a conventional aerosol container with Freon 11 (trichlorofluoromethane) and Freon 12 (dichlorodifluoromethane) propellant system. The composition was easily expelled from the package. Further, the container and contents did not exhibit corrosion or instability even after several months.

EXAMPLE 3

A composition was formed in the same manner as described in Example 1 above from 8 parts Gantrez ES-425, 0.5 part zinc stearate and ethanol to make 100 parts of composition.

The sample was tested in the same manners as described in Example 1 and gave 87.3% curl retention after 1 hour, very good moisture resistance, was easily removed by a commercial shampoo, but the film was hazy.

EXAMPLE 4

A composition was formed in the same manner as described in Example 1 above from 4 parts copolymer of poly(hexane/maleic anhydride half ethyl ester) of 1 to 1 monomer ratio of moderate molecular weight; 0.9 parts zinc neodecanoate and ethanol to make 100 parts of composition.

The sample was tested in the same manners as described in Example 1 with the following results:
Curl retention: 91.5%
Film: Clear, glossy
Easily removed by both basic and acidic commercial hair shampoos.

EXAMPLE 5

A composition similar to that of Example 4 above is formulated in the same manner described therein except that the resin is a copolymer of poly(propylene/maleic anhydride half ethyl ester) of moderate molecular weight. Monomer ratio of about 1 to 1. The composition is tested in the same manner as described in Example 1 and gives substantially the same results as described for the composition of Example 4.

EXAMPLE 6

A composition similar to Example 1 is formed except that the zinc salt is substituted by magnesium neodecanoate. The composition is tested in the same manner as described in Example 1 and gives substantially the same results.

EXAMPLES 7 AND 8

Compositions were formulated of the following components in the manner described in Example 1 above.

|  | EXAMPLE 7 | EXAMPLE 8 |
|---|---|---|
| Gantrez ES-425 | 8 | 8 |
| Mg Stearate | 0.45 | 1.15 |
| Ethanol | qs. | qs. to 100 |
| Curl Retention | 89.4 | 84.5 |
| Moisture Resistance | Excellent | Excellent |
| Film | Glossy; sl. haze | Glossy; sl. haze |
| Washable in H$_2$O/Shampoo | Yes | Yes |
| Room Temp. Dry | Yes | Yes |
| Tack Free | Yes | Yes |

EXAMPLES 9 AND 10

Compositions were formed of the following components in the manner described in Example 1 above:

|  | Ex. 9 | Ex. 10 |
|---|---|---|
| Composition |  |  |
| Gantrez ES-425 | 8 | 8 |
| Zinc 2-ethyl hexanoate | 0.7 | 1.4 |
| Ethanol | qs. | qs. to 100 |
| Properties |  |  |
| Moisture Resistance | Excellent | Good |
| Film | Clear;glossy | Clear;glossy |
| H$_2$O/Shampoo Washable | Yes | Yes |
| Room Temp. Dry | Yes | Yes |
| Tack Free | Yes | Yes |

EXAMPLE 11

A composition is formed in the same manner as Example 1 except that the resin is substituted with a copolymer of poly (vinyl acetate/crotonic acid). The composition has similar properties to that exhibited by the composition of Example 1.

EXAMPLE 12

The compositions of Examples 3 to 11 are packaged in a conventional aerosol container using Freon 11 and Freon 12 as propellant. The contents expel easily and do not exhibit corrosion with the container or instability.

EXAMPLE 13

A composition was formed for use in a hand-activated spray bottle comprising 8 parts (Gantrez ES-425; 1.35 parts zinc neodecanoate; 7 parts water and ethanol to 100 parts. The composition was formed in the same manner as described in Example 1 and tests showed 91.7% curl retention; good moisture resistance; clear glossy film obtained; and easily removable by acid or alkaline shampoo.

While the invention has been described in connection with the preferred embodiment, it is not intended to limit the invention to the particular form set forth above, but, on the contrary, it is intended to cover such alternatives, modifications, and equivalents as may be included within the spirit and scope of the invention as defined by the appended claims.

What is claimed is:

1. A hair setting resin composition comprising an alcoholic medium containing substantially uniformally dispersed therein in an amount sufficient to form a hair retaining film of a film-forming resin selected from the group consisting of (1) a copolymer of a vinyl alkyl ether and a C$_1$-C$_5$ alkyl half-ester of maleic anhydride, (2) a C$_2$-C$_6$ alkene/maleic anhydride half-C$_1$-C$_5$ ester copolymer, and (3) a copolymer of a vinyl ester and acrylic acid or an alpha or beta-substituted acrylic acid wherein said substituent is hydrogen or a single C$_1$-C$_3$ alkyl, and a polyvalent metal C$_5$-C$_{20}$ alkyl carboxylic acid salt capable of forming a stable, non-toxic, clear, glossy film with said resin; the anhydride or acid being used in an amount sufficient to form said resin to contain at least 5 percent by weight of free carboxylic acid groups therein; the amount of salt being sufficient to contain a stoichiometric ratio of metal to free polymeric carboxyl group of from about 1 to 10 to less than 1 to 1; the resultant pH of the composition being between about 3.5 and 7.5.

2. The hair setting composition of claim 1 having a pH of between about 4 and 6.

3. The hair setting composition of claim 2 wherein the polyvalent metal is calcium, zirconium, magnesium, or zinc.

4. The hair setting composition of claim 3 wherein the polyvalent metal salt of the monocarboxylic acid is present in an amount to attain a stoichiometric ratio of metal to free polymeric carboxylic acid of between about 1 to 10 to 1 to 2 and wherein the alcoholic medium is C$_1$-C$_8$ alcohol.

5. The hair setting composition of claim 4 wherein the resin is a copolymer of C$_1$-C$_3$ alkyl half-ester of maleic anhydride and vinyl methyl ether.

6. The hair setting composition of claim 4 wherein the resin is a copolymer of a C$_1$-C$_6$ alkene/maleic anhydride half C$_1$-C$_3$ alkyl ester copolymer.

7. The hair setting composition of claim 4 wherein the metal salt is a zinc C$_5$-C$_{20}$ alkyl carboxylate.

8. The hair setting composition of claim 7 wherein the zinc carboxylate is selected from the group consisting of the zinc salts of stearic, 2-octyl-dodecanoic, 2-ethylhexanoic, and neodecanoic acids.

9. An aerosol hair setting composition comprising the composition of claim 1 and an aerosol propellant.

10. The composition of claim 9 wherein the aerosol propellant contains at least one halogenated hydrocarbon.

11. An aerosol composition comprising the composition of claim 4 in combination with an aerosol propellant.

12. The composition of claim 11 wherein the aerosol propellant contains at least one halogenated hydrocarbon.

13. An aerosol composition comprising the composition of claim 7 in combination with an aerosol propellant.

14. The composition of claim 13 wherein the aerosol propellant contains at least one halogenated hydrocarbon.

15. The method of shaping human hair comprising forming the hair into the desired configuration and applying an effective amount to form a hair retaining film of the composition of claim 1 thereto.

16. The method of shaping human hair comprising shaping the human hair into the desired configuration and applying an effective amount to form a hair retaining film of the composition of claim 4.

17. The method of shaping human hair comprising shaping the human hair into the desired configuration and applying an effective amount to form a hair retaining film of the composition of claim 7.

18. The composition of claim 1 in which the alcoholic medium contains, in addition, up to about 10% by weight water.

19. The composition of claim 4 in which the alcoholic medium contains, in addition, up to about 10% by weight water.

20. The composition of claim 7 in which the alcoholic medium contains, in addition, up to about 10% by weight water.

* * * * *

UNITED STATES PATENT AND TRADEMARK OFFICE
CERTIFICATE OF CORRECTION

PATENT NO. : 4,036,241
DATED : July 19, 1977
INVENTOR(S) : GERHART KARG and CHRISTOPHER D. VAUGHAN It is certified that error appears in the above-identified patent and that said Letters Patent are hereby corrected as shown below:

Column 7, line 42, "(" should be omitted.

Column 7, line 62, the word "alkyl" should be inserted between "$C_5$" and "ester"

Signed and Sealed this

Seventh Day of February 1978

[SEAL]

Attest:

RUTH C. MASON
Attesting Officer

LUTRELLE F. PARKER
Acting Commissioner of Patents and Trademarks